US005853766A

United States Patent [19]
Goettsche et al.

[11] Patent Number: 5,853,766
[45] Date of Patent: *Dec. 29, 1998

[54] WOOD PRESERVATIVES

[75] Inventors: Reimer Goettsche; Hans-Volker Borck, both of Baden-Baden, Germany

[73] Assignee: Dr. Wolman GmbH, Sinzheim, Germany

[*] Notice: The term of this patent shall not extend beyond the expiration date of Pat. No. 5,635,217.

[21] Appl. No.: 785,084

[22] Filed: Jan. 21, 1997

Related U.S. Application Data

[63] Continuation of Ser. No. 329,425, Oct. 24, 1994, Pat. No. 5,635,217, which is a continuation of Ser. No. 860,155, Mar. 30, 1992, abandoned.

[30] Foreign Application Priority Data

Apr. 18, 1991 [DE] Germany ........................ 41 12 652.1

[51] Int. Cl.$^6$ ........................ A01N 43/653; A01N 59/20; A01N 57/00
[52] U.S. Cl. ........................ 424/632; 424/630; 424/633; 424/634; 424/635; 424/637; 424/638; 424/DIG. 11; 106/18.31; 106/18.32; 514/75; 514/383; 514/642; 514/643; 514/500
[58] Field of Search ........................ 424/632, 630, 424/633, 634, 635, 637, 638, DIG. 11; 514/75, 383, 642, 643, 500; 106/18.31, 18.32

[56] References Cited

U.S. PATENT DOCUMENTS

| | | | |
|---|---|---|---|
| 3,625,738 | 12/1971 | Donaldson et al. | |
| 3,976,594 | 8/1976 | Dahlgren. | |
| 4,160,838 | 7/1979 | Van Reet et al. | 514/383 |
| 5,094,890 | 3/1992 | Smith et al. | |
| 5,527,384 | 6/1996 | Williams et al. | 106/18.32 |
| 5,634,967 | 6/1997 | Williams et al. | 106/18.32 |
| 5,635,217 | 6/1997 | Goettsche et al. | 424/632 |

FOREIGN PATENT DOCUMENTS

| | | |
|---|---|---|
| 81 35 221/78 | 10/1979 | Australia. |
| 76861/81 | 5/1982 | Australia. |
| 30157/84 | 1/1985 | Australia. |
| 58463/86 | 6/1986 | Australia. |
| 70428/87 | 9/1987 | Australia. |
| B-66642/86 | 8/1989 | Australia. |
| 64786/90 | 4/1991 | Australia. |
| 1284854 | 6/1991 | Canada. |
| 0 050 738 | 5/1982 | European Pat. Off.. |
| 0 052 424 | 5/1982 | European Pat. Off.. |
| 0089958 | 10/1983 | European Pat. Off.. |
| 89958 | 10/1983 | European Pat. Off.. |
| 0 102 540 | 3/1984 | European Pat. Off.. |
| 0102 093 | 3/1984 | European Pat. Off.. |
| 0109 354 | 5/1984 | European Pat. Off.. |
| 0234 461 | 9/1987 | European Pat. Off.. |
| 0238 051 | 9/1987 | European Pat. Off.. |
| 0252 366 | 1/1988 | European Pat. Off.. |
| 0 393 746 | 10/1990 | European Pat. Off.. |
| 2 562 903 | 10/1985 | France. |

WO 82/03817 11/1982 WIPO.

OTHER PUBLICATIONS

The Royal Society of Chemistry, 1991, "The Chemistry of Wood Preservation", pp. 1–33 and 101–116.
Dictionary of Organic Compounds, Fifth edition, vol. 5, pp. 5388–5389 (1983).
22nd Forest Products Research Conference, Nov. 1986, vol. 1, C.W. Chin, et al., "Recent Advances in Oil–Based Preservatives Emulsions in Australia", pp. 1–13.
21st Forest Products Research Conference, Nov. 1984, vol. 1, C.W. Chin, et al., "Pigment Emulsified Creosote—An Alternative To High Temperature Creosote", pp. 1–8.
Holzforschung, vol. 45, 1991, No. 1, pp. 19–22, "An Accelerated Field Simulator Trial Of Metal Soaps", L.J. Cookson, et al.
J. Inst. Wood Sci., (1988) 11(3), pp. 103–107, H. Greaves, et al., "Laboratory Tests On Light–Organic Solent Preservatives For Use In Australia 2 Assessments Of Further Candidate Fungicides".
The International Journal of Wood Preservation, vol. 2, No. 1, 1992, "Laboratory Tests On Light Organic Solvent Preservatives for Use In Australia 1. Evaluation of Candidate Fungicides, Including Some Commercial Formulations", H. Greaves, et al., pp. 21–27.
"Wood Pulping With Mono–, Di– and Triethanolamine", A.F.A. Wallis, May 1978, vol., 31, No. 6, 8 pages.
The Chemistry of Wood, 1975, B.L. Browning, p. 430.
Advanced Inorganic Chemistry, A Comprehensive Text, F. Albert Cotton, et al., 1962, p.756.
J. Inst. Wood Sci. (1988), 11 (4), "Laboratory Tests On Light Organic Solvent Preservatives For Use In Australia", H. Graves, et al., pp. 145–148.
Pesticide Index, p. 163 (1990), The Royal Society of Chemistry, Nottingham, England.
The Quick Guide, 985, B.G. Page, et al., p.108.
The Pesticide Manual, A World Compendium, Eighth Edition, 1987, p. 714, "Propiconazole".
Preservative Treatment For Sawn Timber, Venner and Plywood, AS 1604–1980, p. 13 (1980).
Wood Preservation in Australia, No. 438, 1984, Harry Greaves, pp. 54–55.
Proceedings Tenth Forest Products Research Conference, Jul. 1961, 86–109.
The Chemistry Of Wood Preservation, "Wood Preservation: The Biological Challenge", 1991, D.J. Dickinson, pp. 1–33, 69–87, 101–116.
The International Research Group on Wood Preservation, Document No.: IRG/WP/3529, "Suitability Of Propiconazole (R 49362) As A New–Generation Wood–Preserving Fungicide", Alex Valcke, Mar. 17, 1989, pp. 1–17.

(List continued on next page.)

Primary Examiner—John Pak
Attorney, Agent, or Firm—Oblon, Spivak, McClelland, Maier & Neustadt, P.C.

[57] ABSTRACT

Wood preservatives contain a copper compound, an alkanolamine, a triazole, an emulsifier and/or a phosphonium compound and are used for impregnating wood.

32 Claims, No Drawings

U.S. PATENT DOCUMENTS

The International Research Group on Wood Preservation, Doc. No.: IRG/WP/3629, "Tebuconazole A New Triazole Fungicide For Wood Preservation", Roland Grundlinger, et al., Apr. 23, 1990, pp. 1–3.

The International Research Group on Wood Preservation, Document No.: IRG/WP/3634, "Tebuconazole, A New Wood–Preserving Fungicide", Bettina Wüstenhöfer, et al., May 7, 1990, pp.1–21.

Physical Chemistry, P. W. Atkins, 2nd Edition, 1982, pp. 842–843.

*Materials and Organisms*, 1986, vol. 21, pp. 251–264, "An In–ground Natural Durability Field Test of Australian Timbers and Exotic Reference Species", Gary C. Johnson, John D. Thornton and Ian W. Sauders.

*Materials and Organisms*, 1991, vol. 26, pp. 303–315,"An Australian test of wood preservatives", Gary C. Johnson and Johnson D. Thornton.

The Merck Index, 10th edition, Rahway (NJ), Merck & Co., Inc. 1983, p.377.

The Agrochemicals Handbook, second edition, Mottingham (England), 1987, The Royal Society of Chemistry, p. A347/ Aug. 87.

WOOD PRESERVATIVES

This is a continuation of application Ser. No. 08/329,425 filed on Oct. 24, 1994, now U.S. Pat. No. 5,635,217, which is a continuation of application Ser. No. 07/860,155, filed on Mar. 30, 1992, abandoned.

Wood preservatives based on inorganic copper compounds with alkanolamines as complexing agents are known (European Patent 89,958). Despite high copper contents, the activity of these agents against wood-destroying Basidiomycetes is insufficient in comparison with known copper- and chromate-containing salts having a comparable copper content.

It has now been found that wood preservatives based on copper compounds and alkanolamines, which contain a triazole compound and an emulsifier or which contain a phosphonium compound, have very good activity against wood-destroying Basidiomycetes. The present invention relates to mixtures which contain a triazole compound and an emulsifier, to mixtures which contain a phosphonium compound and to mixtures which contain a triazole compound, an emulsifier and a phosphonium compound.

In spite of the content of copper compounds in the wood preservative, on dilution with water the triazole compounds form a clear emulsion. The advantage of the novel agents is that triazole compounds which are insoluble in water are present in the novel agents in the the form of aqueous emulsions or clear aqueous concentrates. Clear aqueous liquids are formed on dilution with water.

Homogeneous concentrates can be obtained by adding small amounts of organic solvents to the wood preservative, for example alcohols (ethanol or isopropanol), glycols (ethylene glycol or propylene glycol), glycol ethers (ethylene glycol monomethyl ether or ethylene glycol monoethyl ether), glycol ether esters (butylglycol acetate), dimethylformamide or N-methyl-pyrrolidone. The solvents additionally act as solubilizers for the triazoles. With the additional use of arylcarboxylic acids, cycloalkylcarboxylic acids or aliphatic $C_5$–$C_{20}$-mono- or dicarboxylic acids or corresponding amine, alkali metal or copper salts, however, the use of solvents can be reduced to a minimum for obtaining homogeneous concentrates.

The copper compounds can be used as water-soluble or water-insoluble compounds, for example copper sulfate, copper acetate, copper hydroxide, copper oxide, copper borate, copper fluoride or basic copper carbonate.

An alkanolamine is, in particular, monoethanolamine; the use of other alkanolamines, for example isopropanolamine, 1,1- or 1,2-diaminoethanol, aminoethylethanolamine, diethanolamine, triethanolamine or methylethanolamine, is possible.

The amount of added alkanolamines is advantageously such that a pH of 7 or more, preferably from 8.5 to 10.5, is established in the dilute aqueous impregnating solution. The amount of amines should be sufficient for complexing the copper (1 g atom of copper requires about 4 mol equivalents of amine).

A triazole compound is, for example, 1-(2-(2-4-dichlorophenyl)-4-methyl-1,3-dioxolan-2-yl-methyl)-1H-1,2,4-triazole, 1-(2-(2,4-dichlorophenyl)-1,3-dioxolan-2-yl-methyl)-1H-1,2,4-triazole (azaconazole), 1-(2-(2,4-dichlorophenyl)-4-ethyl-1,3-dioxolan-2-yl-methyl)-1H-1,2,4-triazole, 1-(2-(2,4-dichlorophenyl)-4-propyl-1,3-dioxolan-2-yl-methyl)-1H-1,2,4-triazole (propiconazole), 1-(2-(2,4-dichlorophenyl)-4-phenyl-1,3-dioxolan-2-yl-methyl)-1H-1,2,4-triazole or α-tert-butyl-a-(p-chlorophenylethyl)-H-1,2,4-triazole-1-ethanol (tebuconazole).

An emulsifier is, for example, an anionic, cationic or nonionic emulsifier or a mixture thereof. Nonionic emulsifiers are, for example, adducts of ethylene oxide (EO) or propylene oxide or mixtures thereof with organic hydroxy compounds, for example alkylphenols, fatty acids, fatty alcohols and mixtures thereof. Examples of suitable cationic emulsifiers are quaternary ammonium compounds and/or salts of fatty amines (for example dimethyl-($C_{12}$–$C_{14}$)-alkylamines).

A quaternary ammonium compound is, for example, a compound of the general formula $R^1R^2R^3R^4N^+Z^-$, where $R^1$ is alkyl of 8 to 20 carbon atoms, in particular alkyl of 12 to 20 carbon atoms or benzyl which is unsubstituted or substituted by $C_1$–$C_{20}$-alkyl or halogen, $R^2$ is $C_1$–$C_6$-alkyl, $C_3$–$C_9$-alkoxyalkyl or polymeric ethylene oxide (EO) or propylene oxide (PO) where the number of EO or PO units n is from 2 to 50, $R^3$ is $C_1$–$C_6$-alkyl, $C_3$- or $C_4$-alkoxy or polymeric ethylene oxide (EO) or propylene oxide (PO) where the number of EO or PO units n is from 2 to 50 and $R^4$ is $C_1$–$C_{20}$-alkyl, or two of the radicals $R^1$ to $R^4$, together with the nitrogen atom, form a heterocyclic radical which contains 4 or 5 carbon atoms and one, two or three double bonds, the carbon atoms being unsubstituted or substituted by $C_1$–$C_4$-alkyl or halogen, and Z is an acid radical, eg. halide.

Particularly suitable phosphonium compounds are compounds of the formula $$R^1{}_3R^2P^+Y^-$$

where $R^1$ is alkyl of 1 to 6 carbon atoms, hydroxyalkyl of 1 to 6 carbon atoms or phenyl, $R^2$ is alkyl of 8 to 18 carbon atoms and Y is an acid radical, in particular a halide anion.

$R^1$ and $R^2$ are preferably straight-chain.

The quaternary phosphonium compounds may be present individually or as mixtures in the novel concentrates. Examples of such phosphonium compounds are trimethyl-n-dodecylphosphonium chloride, triethyl-n-decylphosphonium bromide, tri-n-propyl-n-tetradecylphosphonium chloride, trimethylol-n-hexadecylphosphonium chloride, tri-n-butyl-n-tetradecylphosphonium chloride, tri-n-butyl-n-dodecylphosphonium bromide, tri-n-butyl-n-decylphosphonium chloride, tri-n-butyl-n-hexadecylphosphonium bromide, tri-n-hexyl-n-decylphosphonium chloride, triphenyl-n-dodecylphosphonium chloride, triphenyl-n-tetradecylphosphonium bromide and triphenyl-n-octadecylphosphonium chloride.

Aliphatic carboxylic acids can be added to improve the homogeneity of the concentrates. Examples of such acids are propionic acid, hexanoic acid, heptanoic acid, branched carboxylic acids, eg. -ethylenehexanoic acid or isooctanoic acid, neocarboxylic acids, aliphatic dicarboxylic acids, eg. sebacic acid, cycloalkylcarboxylic acids, eg. cyclohexanoic acid, and arylcarboxylic acids, eg. benzoic acid or 3- or 4-hydroxybenzoic acid.

When the abovementioned acids are used, it is advantageous in some cases to improve the penetration of the wood preservative in large scale industrial processes by adding complex-forming, polymeric nitrogen compounds, eg. polyethyleneimines.

Polyethyleneimines (PEI, polymin) are known and are formed by polymerization of 1,2-ethyleneimine. They contain the nitrogen in primary (terminal group), secondary or tertiary (branching) form. Polyethyleneimines where n is greater than 10 are suitable; very good results are obtained when PEI having a degree of polymerization n between 50 and 1,000 are used.

The wood preservatives may, if required, contain further compounds, for example compounds having a fungicidal anion, such as a boron compound (for example alkali metal borate, aminoborate, boric acid or boric ester) and fluorides (for example potassium fluoride and/or salts of fluoboric acid and/or fluophosphoric acid and/or difluophosphoric acid).

The action spectrum of the novel wood preservatives can, if required, be improved by adding further active ingredients. Examples of suitable compounds are N-organodiazeniumdioxy compounds, organotin compounds, in particular tributyltin (TBT) compounds and isothiazoline compounds of the following formula

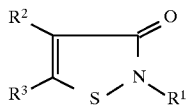

where $R^1$ is hydrogen, an alkyl, alkenyl or alkynyl radical of 1 to 18 carbon atoms, cycloalkyl having a $C_3$–$C_5$-ring and not more than 12 carbon atoms or an aralkyl or aryl radical of not more than 19 carbon atoms and $R^2$ and $R^3$ independently of one another are hydrogen, halogen or $C_1$–$C_4$-alkyl, or $R^2$ and $R^3$ are part of an aromatic radical.

It is also possible to add further fungicides or insecticides, for example in emulsified form, such as N-tridecyl-2,6-dimethylmorpholine (tridemorph) and/or 4-(3-para-tert-butylphenyl)-2-methyl-propyl-2,6-cis-dimethylmorpholine (fenpropimorph) and/or chlorinated phenols tetrachloroisophthalodinitrile N-cyclohexyl-N-methoxy-2,5-dimethylfuran-3-carboxamide N-dimethyl-N'-phenyl-(N-fluoromethylthio)-sulfamide N,N-dimethyl-N'-toluyl-(N-fluoromethylthio)-sulfamide methyl benzimidazole-2-carbamate 2-thiocyanomethylthiobenzothiazole 2-iodobenzanilide 1-(1',2',4'-triazol-1'-yl)-1-(4'-chlorophenoxy)-3,3-dimethylbutan-2-one 1-(1',2',4'-triazol-1'-yl)-1-(4'-chlorophenoxy)-3,3-dimethylbutan-2-ol hexachlorocyclohexane O,O-diethyldithiophosphorylmethyl-6-chlorobenzoxazolone 2-(1,3-thiazol-4-yl)-benzimidazole N-trichloromethylthio-3,6,7,8-tetrahydrophthalimide N-(1,1,2,2-tetrachloroethylthio)-3,6,7,8-tetrahydrophthalamide N-trichloromethylthiophthalimide 3-iodo-2-propylbutyl carbamate O,O-dimethyl S-(2-methylamino-2-oxoethyl) dithiophosphate O,O-dimethyl O-(3,5,6-trichloro-2-pyridyl) thiophosphate O,O-dimethyl S-(N-phthalimido)-methyl dithiophosphate O,O-diethyl O-(α-cyanobenzylideneamino) thiophosphate 6,7,8,9,10-hexachloro-1,5,5a,6,9,9a-hexahydro-6,9-methano-2,3,4-benzodioxothiepene 3-oxide (4-ethoxyphenyl)-(dimethyl)-3-(4-fluoro-3-phenoxyphenyl)-propyl silane 2-sec-butylphenyl N-methylcarbamate 2-propoxyphenyl N-methylcarbamate 1-naphthyl N-methylcarbamate norbornene dimethanohexachlorocyclosulfite 1-(4-chlorophenyl)-3-(2,6-difluorobenzoyl)-urea synthetic pyrethroids, such as 3-phenoxybenzyl (+)-3-(2',2-dichlorovinyl-2,2-dimethyl)-cyclopropane-1-carboxylate α-cyano-3,3-phenoxybenzyl 3-(2,2-dichlorovinyl-2,2-dimethyl)-cyclopropane-1-carboxylate 3-(2,2-dibromovinyl-2,2-dimethyl)-α-cyano-m-phenoxybenzyl (1R,3R)-cyclopropanecarboxylate (deltamethrin) α-cyano-3-phenoxybenzylisopropyl-2,4-chlorophenyl acetate.

In concentrated form, the water-dilutable wood preservatives generally contain the copper, for example, in an amount of from 1.0 to 15.0% by weight, calculated as metal.

Suitable concentrates consist of, for example, from 2.50 to 45%, in particular 10 to 20%, of copper compounds, from 5.00 to 50%, in particular 20 to 40%, of alkanolamine, from 0.25 to 15%, in particular 1 to 10%, of triazole compounds, from 2.50 to 40%, in particular 10 to 20%, of phosphonium compounds, from 0.5 to 30%, in particular 5 to 15%, of an emulsifier, from 0 to 40% of a compound having a fungicidal inorganic or organic anion, from 0 to 40% of an organic solvent, from 0 to 40% of an aliphatic mono- or dicarboxylic acid and/or cycloalkylcarboxylic acid and/or cycloarylcarboxylic acid and from 0 to 15% of a complex-forming, polymeric nitrogen compound, the sum being 100% by weight in each case, and, if required, minor amounts of other components, for example ammonia, corrosion inhibitors, complex-forming acids (eg. nitrilotriacetic acid or ethylenediaminetetraacetic acid where water of relatively high hardness is used) and, if required, water, the amount of which however can generally be kept small and which essentially serves handling purposes.

In addition to the wood preservatives (concentrates), the present invention also relates to the impregnating solutions of correspondingly lower individual concentration which can be prepared by diluting the concentrates with water. The application concentration corresponds to, for example, from 0.01 to 1.50% by weight of metal, eg. copper, in the aqueous impregnating solution, depending on the method of impregnation and the level of risk to which the wood to be impregnated is exposed.

Dissolving the copper salts, if necessary with heating, in the alkanolamines, with or without the addition of acid, water or solvents, and subsequent addition of the emulsifier, the triazole compounds and/or phosphonium compounds result in the formation of highly concentrated pastes, liquid concentrates or two-phase mixtures which, after dilution with water, can be used for impregnating wood. They give a clear liquid in water, even at a high concentration.

The impregnating solution can be used for preserving wood by manual methods, such as spraying, brushing on, immersion or trough impregnation, or by large-scale industrial processes, such as the pressure process, alternating pressure process or double vacuum process. Wood is understood both as solid wood and as woodworking materials, such as particle boards or plywood; here, the wood preservative may also be introduced in the glue mixing process.

The degree of fixing of the copper in the novel preservatives is high; it is more than 90% when large scale industrial methods are used.

The concentrates or solutions can be colored by water-soluble or water-emulsifiable dyes and/or pigment preparations.

Wax, paraffin and/or acrylate dispersions may be added to achieve a water-repellant effect or to improve the fixing.

The concentrates can, if required, also be incorporated in binder-containing water-dilutable systems (primers or transparent coats).

The Examples which follow illustrate the invention.
Determination of the limit of action against wood-destroying fungi The method is used for determining the preventive action of wood preservatives against wood-destroying fungi.

Identical wooden blocks (5×2.5×1.5 cm) dried to a constant weight at 103° C. are completely impregnated with stepwise amounts of the wood preservative to be tested and are dried, washed thoroughly with water (washing out the active ingredient mixture from the wood) and exposed to attack by cultures of wood-destroying fungi in glass dishes. The nutrient medium used for the fungi is malt agar (containing 4% of malt extract). The destruction of the wood caused by the fungal attack is measured by the weight loss of the wood specimens; a weight loss of 2% or more is evaluated as wood destruction.

A lower active ingredient concentration at which the wood just begins to be destroyed and an upper active ingredient concentration at which no wood destruction is detectable and hence complete wood preservation has been achieved are stated. It is always necessary to start from the upper active ingredient concentration for evaluating a wood preservative in practice.

The determination of the limit of the action against wood-destroying fungi (in kg of active ingredient or mixture of active ingredients per m$^3$ of wood) The result should be understood as follows. The lower the limit, the better the fungicidal action. 1 kg/m$^3$ is thus better than 2 kg/m$^3$.

EXAMPLE A (Not According to the Invention)

20% by weight of Cu(OH)$_2$CuCO$_3$
45% by weight of monoethanolamine
10% by weight of boric acid
25% by weight of water
Limit with respect to the wood-destroying Basidiomycetes
  *Coniophora puteana* and *Poria placenta*: more than 35 kg/m$^3$.

EXAMPLE B (Not According to the Invention)

17.5% of Cu(OH)$_2$.CuCO$_3$
42% of monoethanolamine
30% of boric acid
10.5% of water
Limit with respect to *Coniphora puteana* and *Poria placenta*: more than 35 kg/m$^3$.

EXAMPLE C (Not According to the Invention)

Limits for triazole compounds dissolved in acetone

|  | Azaconazole | Propiconazole |
|---|---|---|
| *Coniophora puteana* | 2.8 to 5.7 | 0.21 to 0.33 kg/m$^3$ |
| *Poria placenta* | 0.9 to 1.5 | 0.57 to 0.91 kg/m$^3$ |

EXAMPLE D (Not According to the Invention)

50% n-tributyltetradecylphosphonium chloride (commercial) dissolved in water
Limits
*Coniophora puteana* 7.7 to 12.3 kg/m$^3$
*Poria placenta* 4.7 to 7.3 kg/m$^3$

EXAMPLE 1

14.0% of Cu(OH)$_2$CuCO$_3$
33.5% of monoethanolamine
7.5% of boric acid
6.0% of propionic acid
19.0% of water
4.0% of propiconazole
10.0% of ethoxylated nonylphenol (10 units of ethylene oxide per nonylphenol unit=EO 10)
6.0% of propylene glycol
Limits
*Coniophora puteana* 3.0 to 4.7 kg/m$^3$
*Poria placenta* 4.7 to 7.3 kg/m$^3$

EXAMPLE 2

14.0% of Cu(OH)$_2$CUCO$_3$
33.5% of monoethanolamine
22.0% of benzoic acid
10.5% of water
4.0% of propiconazole
10.0% of ethoxylated nonylphenol
6.0% of propylene glycol
Limits
*Coniophora puteana* 4.6 to 7.2 kg/m$^3$
*Poria placenta* 4.7 to 7.3 kg/m$^3$

EXAMPLE 3

14.0% of Cu(OH)$_2$CuCO$_3$
33.5% of monoethanolamine
22.0% of benzoic acid
10.5% of water
2.5% of propiconazole
1.5% of azaconazole
10.0% of ethoxylated nonylphenol
6.0% of propylene glycol
Limits
*Coniophora puteana* 4.6 to 7.2 kg/m$^3$
*Poria placenta* 7.3 to 11.2 kg/m$^3$

EXAMPLE 4

14.0% of Cu(OH)$_2$CUCO$_3$
27.0% of monoethanolamine
7.5% of polymin n=150
21.0% of benzoic acid
14.0% of water
4.0% of propiconazole
10.0% of ethoxylated nonylphenol
9.0% of propylene glycol
Limits
*Coniophora puteana* 3.4 to 4.6 kg/m$^3$
*Poria placenta* 4.6 to 7.2 kg/m$^3$

EXAMPLE 5

13% of Cu(OH)$_2$CUCO$_3$
31% of monoethanolamine
20% of benzoic acid
23% of water
13% of tri-n-butyltetradecylphosphonium chloride
Limits
*Coniophora puteana* 11.4 to 18.3 kg/m$^3$
*Poria placenta* 11.5 to 18.1 kg/m$^3$

We claim:

1. A wood preservative comprising:
   i) a copper compound, in an amount fungicidally effective against wood destroying fungi;
   ii) an alkanolamine;
   iii) propiconazole, in an amount fungicidally effective against wood destroying fungi; and iv) an emulsifier.

2. The wood preservative of claim 1, wherein said emulsifier is selected from the group consisting of an anionic emulsifier, a cationic emulsifier, a non-ionic emulsifier and a mixture thereof.

3. The wood preservative of claim 1, wherein said emulsifier is selected from the group consisting of a quaternary ammonium compound, a fatty amine salt and a mixture thereof.

4. The wood preservative of claim 1, wherein said emulsifier is a quaternary ammonium compound.

5. The wood preservative of claim 1, wherein said emulsifier is a quaternary ammonium compound of the formula $$R^1R^2R^3R^4N^+Z^-$$

wherein
- $R^1$ is $C_{8-20}$ alkyl, unsubstituted benzyl, substituted benzyl substituted by $C_{1-20}$ alkyl or halogen;
- $R^2$ is $C_{1-6}$ alkyl, $C_{3-9}$ alkoxyalkyl, polymeric ethylene oxide (EO) or polymeric propylene oxide (PO) where the number of EO or PO units n is from 2 to 50;
- $R^3$ is $C_{1-6}$ alkyl, $C_{3-4}$ alkoxy, polymeric ethylene oxide (EO) or polymeric propylene oxide (PO) where the number of EO or PO units n is from 2 to 50;
- $R^4$ is $C_{1-20}$ alkyl; or
- two of the radicals $R^1$ to $R^4$ together with the nitrogen atom, form a heterocyclic radical which contains 4 or 5 carbon atoms and one, two or three double bonds, the carbon atoms being unsubstituted or substituted by $C_{1-4}$ alkyl or halogen; and Z is an acid radical.

6. The wood preservative of claim 1, further comprising a phosphonium compound in an amount fungicidally effective against wood destroying fungi.

7. A method for preserving wood, which comprises treating the wood with an effective amount of the wood preservative as claimed in claim 1.

8. A wood preservative comprising the product obtained by mixing:
i) a copper compound, in an amount fungicidally effective against wood destroying fungi;
ii) an alkanolamine;
iii) propiconazole, in an amount fungicidally effective against wood destroying fungi; and
iv) an emulsifier.

9. The wood preservative of claim 8, wherein said emulsifier is selected from the group consisting of an anionic emulsifier, a cationic emulsifier, a non-ionic emulsifier and a mixture thereof.

10. The wood preservative of claim 8, wherein said emulsifier is selected from the group consisting of a quaternary ammonium compound, a fatty amine salt and a mixture thereof.

11. The wood preservative of claim 8, wherein said emulsifier is a quaternary ammonium compound.

12. The wood preservative of claim 8, wherein said emulsifier is a quaternary ammonium compound of the formula $$R^1R^2R^3R^4N^+Z^-$$

wherein
- $R^1$ is $C_{8-20}$ alkyl, unsubstituted benzyl, substituted benzyl substituted by $C_{1-20}$ alkyl or halogen;
- $R^2$ is $C_{1-6}$ alkyl, $C_{3-9}$ alkoxyalkyl, polymeric ethylene oxide (EO) or polymeric propylene oxide (PO) where the number of EO or PO units n is from 2 to 50;
- $R^3$ is $C_{1-6}$ alkyl, $C_{3-4}$ alkoxy, polymeric ethylene oxide (EO) or polymeric propylene oxide (PO) where the number of EO or PO units n is from 2 to 50;
- $R^4$ is $C_{1-20}$ alkyl; or
- two of the radicals $R^1$ to $R^4$ together with the nitrogen atom, form a heterocyclic radical which contains 4 or 5 carbon atoms and one, two or three double bonds, the carbon atoms being unsubstituted or substituted by $C_{1-4}$ alkyl or halogen; and Z is an acid radical.

13. The wood preservative of claim 8, further comprising a phosphonium compound in an amount fungicidally effective against wood destroying fungi.

14. A method for preserving wood, which comprises treating the wood with an effective amount of the wood preservative as claimed in claim 8.

15. A wood preservative concentrate comprising:
i) 2.50–45% by weight of said concentrate of a fungicidally effective copper compound;
ii) 5.00–50% by weight of said concentrate of an alkanolamine;
iii) 0.25–15% by weight of said concentrate of propiconazole; and
iv) 0.5–30% by weight of said concentrate of an emulsifier,
wherein said copper, calculated as metal, is present in an amount of from 1.0 to 15.0% by weight of said concentrate.

16. The wood preservative concentrate of claim 15 comprising:
i) 10–20% by weight of said concentrate of said fungicidally effective copper compound;
ii) 20–40% by weight of said concentrate of said alkanolamine;
iii) 1–10% by weight of said concentrate of propiconazole: and
iv) 5–15% by weight of said concentrate of said emulsifier.

17. The wood preservative of claim 15, wherein said emulsifier is selected from the group consisting of an anionic emulsifier, a cationic emulsifier, a non-ionic emulsifier and a mixture thereof.

18. The wood preservative of claim 15, wherein said emulsifier is selected from the group consisting of a quaternary ammonium compound, a fatty amine salt and a mixture thereof.

19. The wood preservative of claim 15, wherein said emulsifier is a quaternary ammonium compound.

20. The wood preservative of claim 15, wherein said emulsifier is a quaternary ammonium compound of the formula $$R^1R^2R^3R^4N^+Z^-$$

wherein
- $R^1$ is $C_{8-20}$ alkyl, unsubstituted benzyl, substituted benzyl substituted by $C_{1-20}$ alkyl or halogen;
- $R^2$ is $C_{1-6}$ alkyl, $C_{3-9}$ alkoxyalkyl, polymeric ethylene oxide (EO) or polymeric propylene oxide (PO) where the number of EO or PO units n is from 2 to 50;
- $R^3$ is $C_{1-6}$ alkyl, $C_{3-4}$ alkoxy, polymeric ethylene oxide (EO) or polymeric propylene oxide (PO) where the number of EO or PO units n is from 2 to 50;
- $R^4$ is $C_{1-20}$ alkyl; or
- two of the radicals $R^1$ to $R^4$ together with the nitrogen atom, form a heterocyclic radical which contains 4 or 5 carbon atoms and one, two or three double bonds, the carbon atoms being unsubstituted or substituted by $C_{1-4}$ alkyl or halogen; and Z is an acid radical.

21. The wood preservative concentrate of claim 15, further comprising a phosphonium compound in an amount fungicidally effective against wood destroying fungi.

22. A clear aqueous wood impregnating emulsion or solution obtained by diluting the concentrate of claim 15 with water.

23. A method for preserving wood, wherein the wood is treated with an effective amount of the wood preservative as claimed in claim 15.

24. A wood preservative concentrate comprising the product obtained by mixing:
   i) 2.50–45% by weight of said concentrate of a fungicidally effective copper compound;
   ii) 5.00–50% by weight of said concentrate of an alkanolamine;
   iii) 0.25–15% by weight of said concentrate of propiconazole; and
   iv) 0.5–30% by weight of said concentrate of an emulsifier,
wherein said copper, calculated as metal, is present in an amount of from 1.0–15.0% by weight of said concentrate.

25. The wood preservative concentrate of claim 24, comprising:
   i) 10–20% by weight of said concentrate of said fungicidally effective copper compound;
   ii) 20–40% by weight of said concentrate of said alkanolamine;
   iii) 1–10% by weight of said concentrate of propiconazole; and
   iv) 5–15% by weight of said concentrate of said emulsifier.

26. The wood preservative of claim 24, wherein said emulsifier is selected from the group consisting of an anionic emulsifier, a cationic emulsifier, a non-ionic emulsifier and a mixture thereof.

27. The wood preservative of claim 24, wherein said emulsifier is selected from the group consisting of a quaternary ammonium compound, a fatty amine salt and a mixture thereof.

28. The wood preservative of claim 24, wherein said emulsifier is a quaternary ammonium compound.

29. The wood preservative of claim 24, wherein said emulsifier is a quaternary ammonium compound of the formula $$R^1R^2R^3R^4N^+Z^-$$

wherein
   $R^1$ is $C_{8-20}$ alkyl, unsubstituted benzyl, substituted benzyl substituted by $C_{1-20}$ alkyl or halogen;
   $R^2$ is $C_{1-6}$ alkyl, $C_{3-9}$ alkoxyalkyl, polymeric ethylene oxide (EO) or polymeric propylene oxide (PO) where the number of EO or PO units n is from 2 to 50;
   $R^3$ is $C_{1-6}$ alkyl, $C_{3-4}$ alkoxy, polymeric ethylene oxide (EO) or polymeric propylene oxide (PO) where the number of EO or PO units n is from 2 to 50;
   $R^4$ is $C_{1-20}$ alkyl; or
   two of the radicals $R^1$ to $R^4$ together with the nitrogen atom, form a heterocyclic radical which contains 4 or 5 carbon atoms and one, two or three double bonds, the carbon atoms being unsubstituted or substituted by $C_{1-4}$ alkyl or halogen;
and Z is an acid radical.

30. The wood preservative concentrate of claim 24, further comprising a phosphonium compound in an amount fungicidally effective against wood destroying fungi.

31. A clear aqueous wood impregnating emulsion or solution obtained by diluting the concentrate of claim 24 with water.

32. A method for preserving wood, wherein the wood is treated with an effective amount of the wood preservative as claimed in claim 24.

* * * * *